(12) United States Patent
Kong et al.

(10) Patent No.: US 7,391,035 B2
(45) Date of Patent: Jun. 24, 2008

(54) METHOD AND DEVICE FOR MONITORING OIL OXIDATION IN REAL TIME BY MEASURING FLUORESCENCE

(75) Inventors: Hosung Kong, Seoul (KR); Eui Sung Yoon, Seoul (KR); Hung Gu Han, Seoul (KR); Lyubov Markova, Gomel (BY); Mikhail Semenyuk, Gomel (BY); Vladimir Makarenko, Gomel (BY)

(73) Assignee: Korea Institute of Science and Technology, Seoul (KR)

(*) Notice: Subject to any disclaimer, the term of this patent is extended or adjusted under 35 U.S.C. 154(b) by 0 days.

(21) Appl. No.: 11/407,404

(22) Filed: Apr. 18, 2006

(65) Prior Publication Data

US 2007/0187617 A1    Aug. 16, 2007

(30) Foreign Application Priority Data

Feb. 14, 2006  (KR)  ...................... 10-2006-0014055

(51) Int. Cl.
*G01N 21/64*  (2006.01)
(52) U.S. Cl. .................................................. 250/461.1
(58) Field of Classification Search ................. 250/364, 250/432, 461.1; 356/70
See application file for complete search history.

(56) References Cited

U.S. PATENT DOCUMENTS

| | | | | |
|---|---|---|---|---|
| 4,814,614 A | * | 3/1989 | Tsui | ............................ 250/301 |
| 5,780,850 A | * | 7/1998 | DeLaune et al. | ............. 250/255 |
| 5,789,665 A | | 8/1998 | Voelker et al. | |
| 5,980,992 A | * | 11/1999 | Kistner et al. | ................ 427/384 |
| 6,459,995 B1 | | 10/2002 | Collister | |
| 6,633,043 B2 | * | 10/2003 | Hegazi et al. | ............. 250/461.1 |
| 6,842,234 B2 | * | 1/2005 | Kong et al. | .................... 356/70 |
| 7,136,155 B2 | * | 11/2006 | Kong et al. | .................... 356/70 |
| 2004/0104355 A1 | * | 6/2004 | DiFoggio et al. | ......... 250/461.1 |
| 2005/0088646 A1 | | 4/2005 | Kong et al. | |

FOREIGN PATENT DOCUMENTS

JP  2002181703 A * 6/2002

* cited by examiner

*Primary Examiner*—David P. Porta
*Assistant Examiner*—David S Baker
(74) *Attorney, Agent, or Firm*—Jones Day

(57) ABSTRACT

There is provided a method and a device of monitoring oil oxidation in real time. The method of the present invention comprises the steps of: irradiating ultraviolet light into oil to be monitored; measuring fluorescence emission intensity of the oil in red, green and blue wavelength bands; determining one value measured in a relatively long wavelength band and the other value measured in a relatively short wavelength band among the fluorescence emission intensity measured in the red, green and blue wavelength bands; calculating a fluorescence emission ratio which is defined as a ratio of the value measured in the relatively long wavelength band to the value measured in the relatively short wavelength band; and monitoring a change in the fluorescence emission ratio. It is then determined whether the fluorescence emission ratio reaches a predetermined critical magnitude. When the fluorescence emission ratio reaches the critical magnitude, the necessity of replacing the oil with new one is indicated.

8 Claims, 10 Drawing Sheets

Mineral oil
(DTE-24)

Synthetic oil
(HF-130)

METHOD AND DEVICE FOR MONITORING OIL OXIDATION IN REAL TIME BY MEASURING FLUORESCENCE

FIELD OF THE INVENTION

The present invention generally relates to devices for monitoring oil oxidation, and more particularly to a device for monitoring oil oxidation capable of being mounted to mechanical devices so as to detect a power of fluorescence emission of oil in real time as an indication of oil oxidation.

BACKGROUND OF THE INVENTION

Chemical and physical analyses of a machine fluid provide information about the condition of the fluid as well as the wear status of the machine using the fluid. Thus, the machine fluid analysis has been widely used for determining lubricant conditions and wear mechanisms in many industries. Further, significant efforts have been made to analyze the condition of the fluid in real time. The real time fluid monitoring mechanism allows the lubricant to be used to its fullest potential with minimized machinery downtime, thereby resulting in increased savings and productivity.

As the oil degrades, the anti-oxidant additive package becomes depleted and the base oil oxidizes. A phenolic inhibitor, which is one of the most common anti-oxidant additives, works to neutralize the free radicals that cause oxidation. Further, aromatic amines, which are also commonly used anti-oxidant additives, work to trap the free radicals. Some anti-wear additives, such as zinc dialkyldithiophosphate (ZDDP), pull double duty as anti-oxidants. The anti-wear additives decompose peroxides formed as a by-product of oxidation and other chemical reactions. Over time, the anti-oxidant additives become depleted until they can no longer effectively protect the base oil.

Oxidation is the major process of the oil degradation, which is caused by the free radical reactions catalyzed by metals and accelerated by heat. The oil oxidation leads to increases in viscosity and acidity, as well as the formation of degradation products such as gum, varnish and sludge.

While the cost of the lubricant itself may be insignificant, the numerous factors for potential collateral damage to the machine are corrosion, varnishing, loss of lubricity, poor demulsibility, filter plugging, etc. Therefore, the oil quality analysis is necessary to increase the lifetime of the machine.

Typically, the lubricant oxidation has been estimated by laboratory detecting methods using a total acid number (TAN), a total base number (TBN) and a Fourier transform infrared (FTIR) analysis.

According to the ASTM (American Standard Test Method) D664, the TAN test employs a potassium hydroxide (KOH) reagent to neutralize acid in the oil. The volume of alkaline reagent required to reach the point of neutralization is a function of the concentration of acid in the oil. The premise is that when the oil oxidizes, organic acids are produced and collected in the oil, thus causing the TAN to rise. The TAN of an oil sample indicates the aging of the oil. Thus, it is typically used to determine when the oil must be changed.

The FTIR analysis effectively measures the concentration of various organic or metallo-organic materials, which are present in the oil. When the oil oxidizes, the hydrocarbon oil molecules become recompounded into soluble and insoluble oxidation by-products. The FTIR analysis measures the accumulation of these by-products at wave numbers of 1800~1670 $cm^{-1}$. However, the above techniques are unacceptable for an on-line oil monitoring system due to their complexity and high cost of equipment.

Various methods and devices for testing the oil quality in real time have been developed and introduced. For example, measuring a dielectric constant change in the lubricant is applied to an oil quality monitoring device. This is achieved by measuring the change in AC impedance, either by measuring the change in frequency when connected in a LC resonant circuit or by measuring the change in the dielectric loss tangent. U.S. Pat. No. 6,459,995 discloses a method and a device for measuring the oil quality based on the permittivity of the oil. The device comprises a capacitive sensor exposed to the oil and an oscillator circuit including a LC or crystal oscillator, which provides an output signal having amplitude dependent upon the loss tangent of the oil. That is, the output of the oscillator varies in response to the changes in the loss of the dielectric medium (oil), which in turn are determined principally by the changes in the oil acidity and polar oxidation products. The change in the amplitude of the oscillator output provides a measure of the oil quality. However, the above method based on the measurement of the dielectric constant is disadvantageous in that it is incapable of recognizing the main reason for the oil degradation—fuel content, water content, oil oxidation or particle contamination.

U.S. Pat. No. 5,789,665 discloses a method and a device for determining the deterioration of lubricating oil in real time based on the measurement of an electrical resistance. The device comprises a sensor employing a polymeric bead matrix layer between two permeable conducting surfaces, which measure the electrical properties of the polymeric matrix. The bead matrix contains a charged ion group that serves as a conducting medium for measuring the solvent properties of the oil. The device further comprises a housing for accommodating a conductive mesh containing small amounts (several milligrams) of ion-charged resin beads. The entire device is immersed in the oil so that the oil can enter into the housing. By using the device, the oil degradation is detected based on a correlation of a relative change in the electrical properties of the beads with a relative change in the solvent properties of the oil. In other words, as the oil changes from a nonpolar (clean) condition to a polar (oxidized contaminated) condition, the interaction between the charged ion groups and the ion-charged resin bead group is also changed. However, the above detecting method has the disadvantages of low reliability and complication of replacing the used polymer beads every time when the degraded oil is changed by new one.

As an alternative to the detecting method, which is based on the measurement of the electrical resistance, several optical techniques (particularly, a fluorescence analysis technique) were proposed to monitor the oil quality in real time. The main problem in applying the fluorescence analysis technique to the oil quality estimation is that there is an influence of high optical oil density on recording the signal of the fluorescence emission. This is because the oil color becomes darkened as the oil is used.

An oil quality monitoring method and a device capable of avoiding such problem is disclosed in U.S. Pat. No. 6,633,043. The method of this patent relates to a time-resolved and laser-induced fluorescence spectroscopy for the characterization and fingerprinting of the oil. This method uses the phenomenon wherein the shapes of the time-resolved fluorescence spectra of the fresh oil and the degraded oil vary in different manners. The method comprises the steps of: exposing an unknown oil sample to a pulse of ultraviolet laser radiation; measuring the intensity of the fluorescence over the spectrum of wavelengths of light of the oil sample at specific narrow time gates within the temporal response of the laser pulse to form a time-resolved spectrum; normalizing the time-resolved spectrum at a particular emission wavelength; plotting the time-resolved spectrum in contours as functions of wavelength and time; comparing the resultant plots of the plotting step with those of similar oil samples taken at known levels of degradation; and determining the condition of the unknown oil sample based on the similarity of the resultant plots with those of the particular known oil sample. The monitoring device comprises a pulsed UV laser for irradiating an oil sample contained in a quartz cuvette. The fluorescence signal of the oil sample is steered by quartz collecting lenses onto entrance slits of a medium-resolution of monochromator for dispersion and is then detected by a photo multiplier mounted at exit slits of the monochromator. The detected fluorescence signal is sent to a signal processor coupled with a gated integrator and is then sampled and digitized according to specific time gates and time gate widths by means of a computer. However, the device is rather complex for on-board realization and further needs expensive equipment.

U.S. Patent Application No. 20050088646 discloses another fluorescent technique taking into account of high optical density of oil. A change in oil fluorescence during the oil oxidation depends on the oil type (its base stock and additives). Although the oil fluorescence increases with the oxidation, the variation in the output signal of a sensor for detecting the fluorescence may be about zero since the increased oil fluorescence can be compensated by the oil absorption. To solve this problem, there is provided a fluorescence detector with two path-lengths, which provide two output signals corresponding to incident optical powers. Based on these two output signals, two parameters—fluorescence emission and optical density of test oil—are estimated simultaneously. However, this technique must use two path-lengths for fluorescence emission measurement and optical density measurement, thereby complicating the detection process and the associated device.

As discussed above, the above prior art devices and methods for monitoring oil oxidation have certain drawbacks and limitations in application.

SUMMARY OF THE INVENTION

It is an object of the present invention to overcome the problems of the prior art and provide a low-cost and simply constructed device for monitoring oil oxidation capable of being mounted to mechanical equipments so as to detect the power of fluorescence emission of oil in real time as an indication of oil oxidation.

Consistent with the foregoing object and in accordance with one aspect of the present invention as embodied herein, there is provided a method of monitoring oil oxidation in real time, comprising the steps of: (a) irradiating ultraviolet light into oil to be monitored; (b) measuring fluorescence emission intensity of the oil in red, green and blue wavelength bands; (c) determining one value measured in a relatively long wavelength band and the other value measured in a relatively short wavelength band among the fluorescence emission intensity measured in the red, green and blue wavelength bands; (d) calculating a fluorescence emission ratio, which is defined as a ratio of the value measured in the relatively long wavelength band to the value measured in the relatively short wavelength band; and (e) monitoring a change in the fluorescence emission ratio in course of oil oxidation.

The method further comprises the steps of: (f) determining whether the fluorescence emission ratio reaches a predetermined critical magnitude; and (g) indicating the necessity of replacing the oil when the fluorescence emission ratio reaches the critical magnitude.

Consistent with the foregoing object, there is provided a device of monitoring oil oxidation in real time, comprising: a housing mounted to a wall of a unit containing oil to be monitored; a transparent optical window disposed in the housing, the optical window having a boundary surface adapted to be in contact with the oil; a light-emitting means for irradiating ultraviolet light into the oil through the optical window; sensing means for detecting fluorescence light emission of the oil and passing through the optical window in red, green and blue wavelength bands, and measuring the fluorescence emission intensity; and a control portion for determining one value measured in a relatively long wavelength band and the other value measured in a relatively short wavelength band among the fluorescence emission intensity measured in the red, green and blue wavelength bands by the sensing means, the control portion being configured to calculate a ratio of the value measured in the relatively long wavelength band to the value measured in the relatively short wavelength band, the control portion being further configured to monitor a change in the ratio.

In accordance with a preferred embodiment of the present invention, the light-emitting means is a UV diode, whereas the sensing means is a color sensor.

In accordance with another preferred embodiment of the present invention, the light-emitting means includes a UV diode and a first optical fiber connected to the light-emitting means. The first optical fiber is adapted to transmit ultraviolet light from the light-emitting means to the optical window. Also, the sensing means includes a color sensor and at least one second optical fiber connected to the color sensor. The second optical fiber is adapted to transmit the fluorescence light emission of the oil and pass through the optical window to the color sensor.

Preferably, the device further comprises a displaying means, which is electrically connected to the control portion. The control portion determines whether the ratio of the value measured in the relatively long wavelength band to the value measured in the relatively short wavelength band reaches a predetermined critical magnitude. If the ratio reaches the critical magnitude, then the control portion operates the displaying means to indicate that the oil needs to be replaced.

BRIEF DESCRIPTION OF DRAWINGS

The above object and features of the present invention will become more apparent from the following description of the preferred embodiments given in conjunction with the accompanying drawings.

DETAILED DESCRIPTION OF THE PRESENT INVENTION

Preferred embodiments of the present invention will now be described with reference to the accompanying drawings.

Figure 1A:
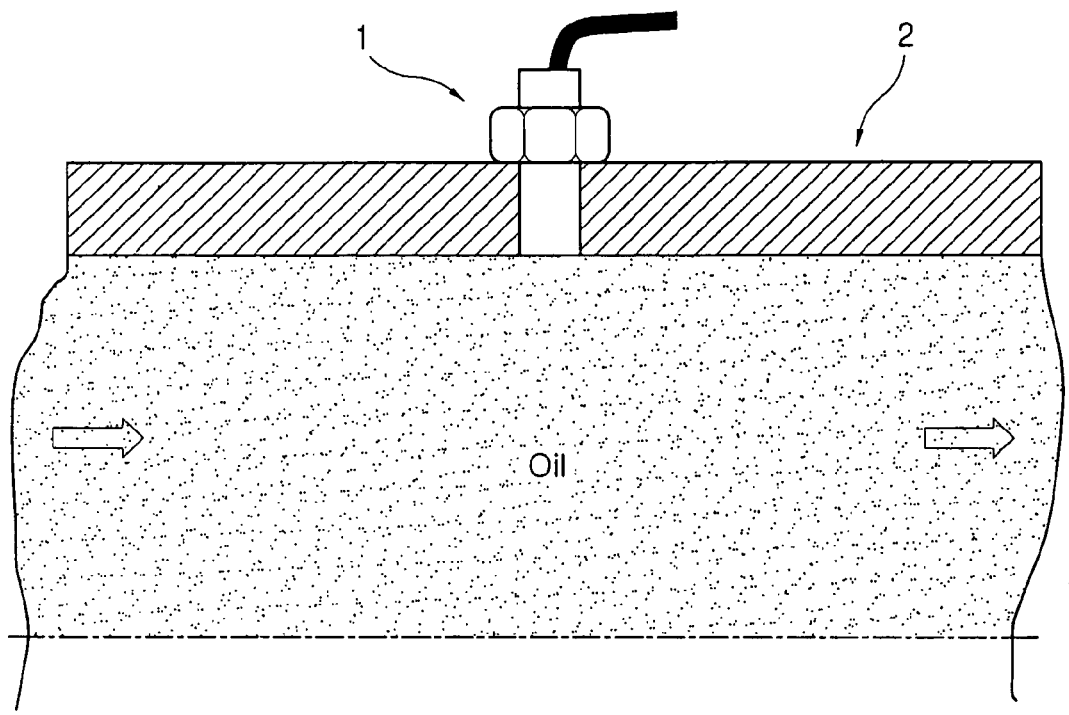
FIG. 1A schematically shows a construction of an oil circulation line equipped with an oil oxidation monitoring device in accordance with the present invention.
Figure 1B:
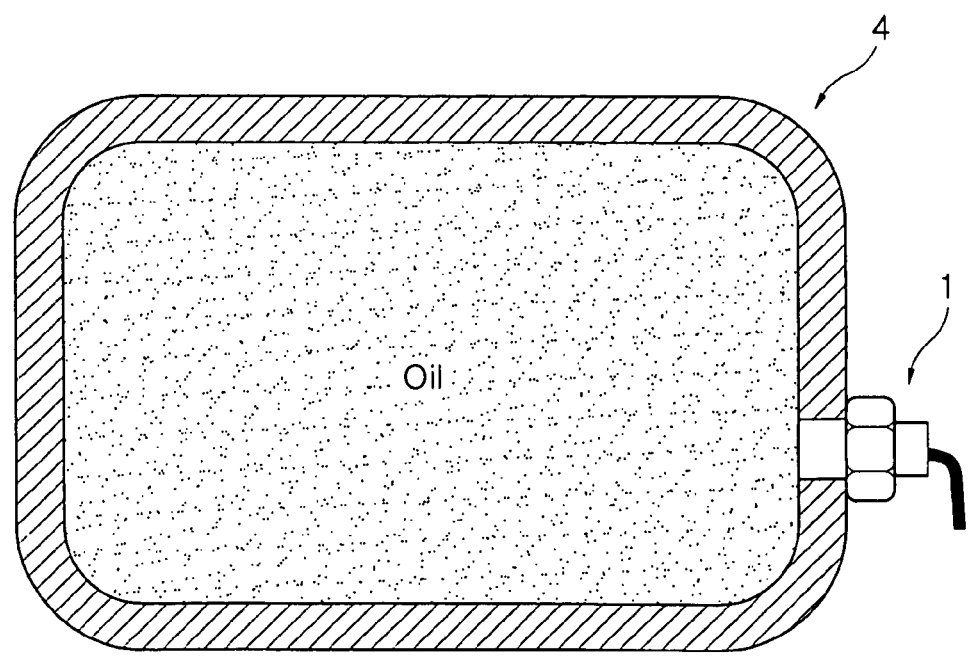
FIG. 1B schematically shows a construction of an oil tank equipped with an oil oxidation monitoring device in accordance with the present invention.

As shown in FIGS. 1A and 1B, an oil oxidation monitoring device 1, which is constructed in accordance with the present invention, can be installed to a wall of an oil circulation line 2 and an oil tank 4 of mechanical equipment.

Figure 2:
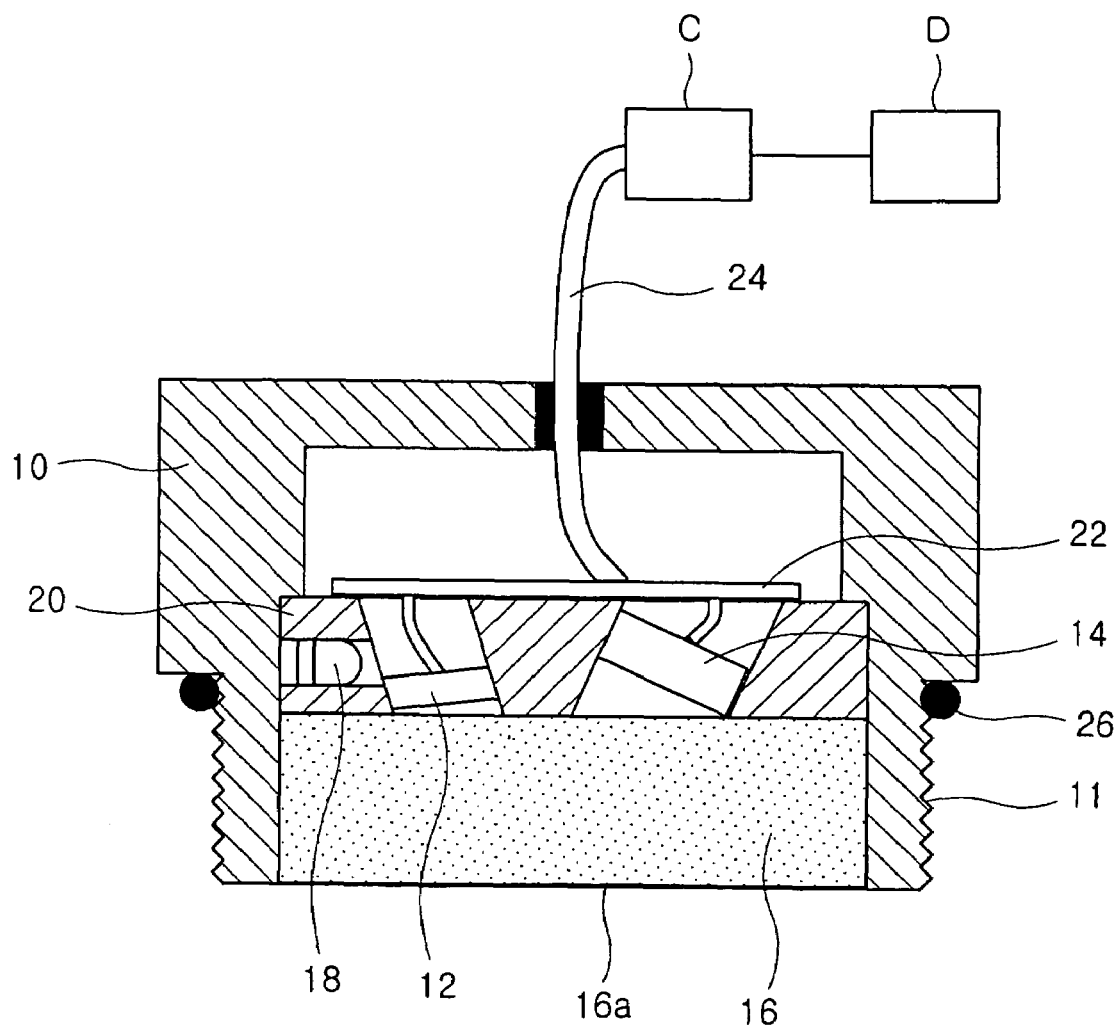
FIG. 2 is a cross-sectional view showing an oil oxidation monitoring device in accordance with a preferred embodiment of the present invention.

FIG. 2 is a cross-sectional view showing an oil oxidation monitoring device, which is constructed in accordance with a preferred embodiment of the present invention.

As shown in the drawing, UV emitting means 12 and color sensing means 14 are provided inside a housing 10. The ultraviolet light from the U emitting means 12 is irradiated into the oil in the oil circulation line or the oil tank through a transparent optical window 16 and induces oil fluorescence. The fluorescence emission of the oil illuminates the color sensing means 14 through the optical window 16. A common available and cheap UV diode with the maximum wavelength of 375~400 nm (e.g., part number "LED3-UV-395-30" manufactured by Bivar Inc.) may be used as the UV emitting means 12. A color sensor (e.g., part number "TCS230" manufactured by Texas Advanced Optoelectronic Solutions Inc.) may be used as the color sensing means 14, which generates three outputs in three spectrum ranges—red, green and blue—corresponding to the fluorescence emission spectrum of the oil. The UV emitting means 12, the color sensing means 14 and the optical window 16 are mounted to a bush 20 fixed inside the housing 10. A photodiode 18 is employed in a feedback circuit (not shown) to stabilize the light of the UV emitting means 12. The photodiode 18, the UV emitting means 12 and the color sensing means 14 are connected to a control portion C by a printed circuit board 22 and a cable 24. A displaying means D is connected to the control portion C for indicating the necessity of replacing the used oil with new one when the control portion C determines that the oil oxidizes beyond the normal condition.

A thread portion 11 is formed around the housing 10 for facilitating the installation of the housing 10 to the oil circulation line or the oil tank. An O-ring 26 is fitted around the housing 10 for preventing the leakage of the oil between the wall of the housing 10 and the wall of the oil circulation line or the oil tank.

An oleophobic material is coated on a boundary surface 16a of the optical window 16 for preventing the adherence of contaminants to the boundary surface 16a. Preferably, the oleophobic material is fluorosilane polymer carried in hydrofluoroether solvent.

Figure 3:
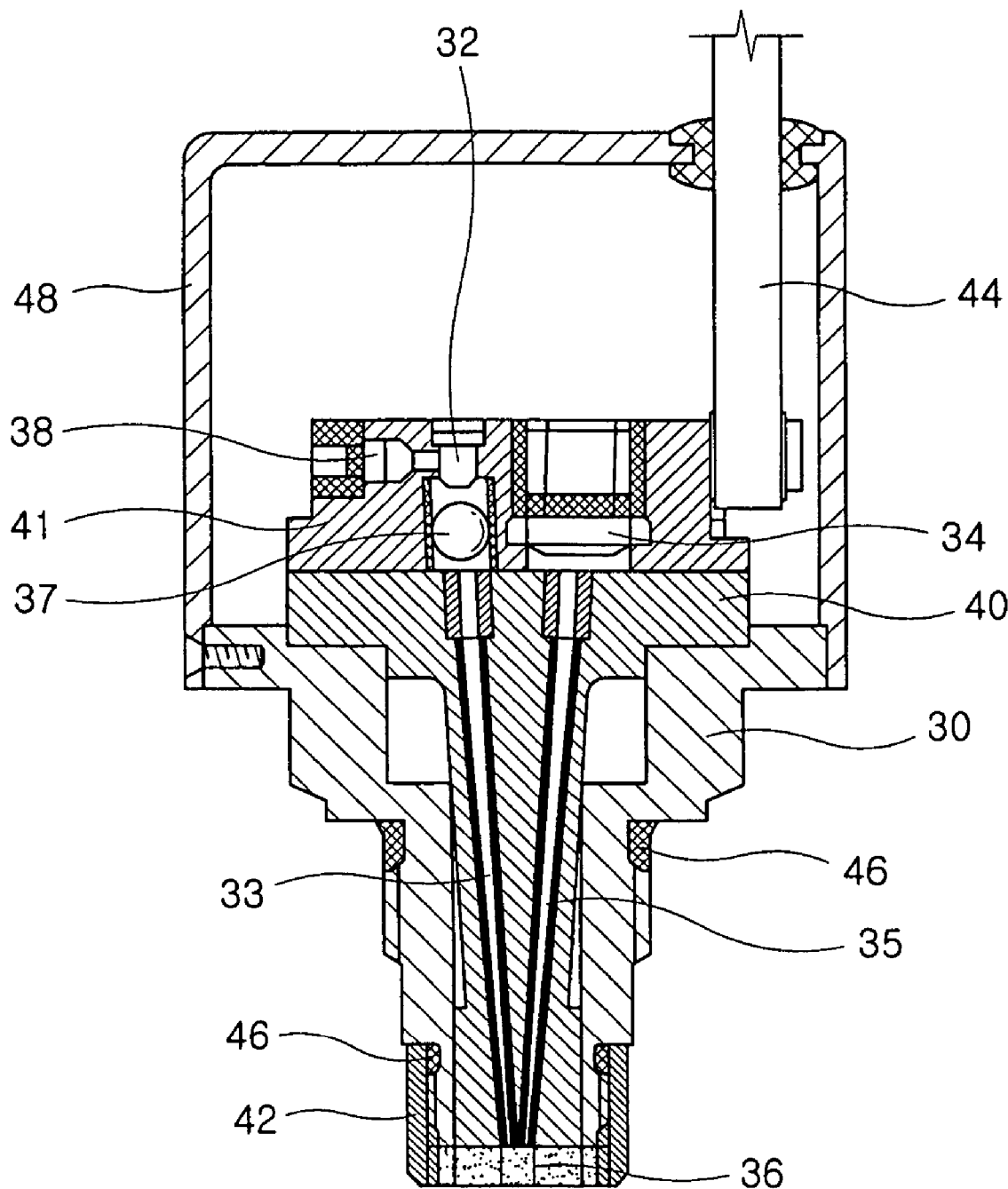
FIG. 3 is a cross-sectional view showing an oil oxidation monitoring device in accordance with another preferred embodiment of the present invention.

FIG. 3 is a cross-sectional view showing an oil oxidation monitoring device in accordance with another preferred embodiment of the present invention. In this embodiment, the UV emitting means includes a UV diode 32 and a first optical fiber 33 extending from the UV diode 32 toward the oil. Further, the color sensing means includes a color sensor 34 and a second optical fiber 35 extending from the color sensor 34 toward the oil. The part number "LED3-UV-395-30" manufactured by Bivar Inc. can be used as the UV diode 32. Also, the 3-element color sensor, such as the part number "MCS3AT" or "MCS3BT" manufactured by MAZeT GmbH, can be used as the color sensor 34.

The ultraviolet light from the UV diode 32 is irradiated into the oil through the first optical fiber 33 and the optical window 36 and induces oil fluorescence. In order to focus the ultraviolet light from the UV diode 32 on an end of the first optical fiber 33, a ball lens 37 is provided between the UV diode 32 and the end of the first optical fiber 33. The first and second optical fibers 33 and 35 are fitted into a holder 40 mounted in a housing 30. The UV diode 32, the color sensor 34 and the ball lens 37 are mounted to a bush 41 coupled on the holder 40. The optical window 36 is fixed to the housing 30 by a nut 42. The fluorescence emission of the oil illuminates the color sensor 34 through the optical window 36 and the second optical fiber 35. A photodiode 38 is employed in a feedback circuit (not shown) to stabilize the light of the UV diode 32. The photodiode 38, the UV diode 32 and the color sensor 34 are connected to a control portion C (see FIG. 2) by a printed circuit board (not shown) and a cable 44. O-rings 46 are fitted around the housing 30 for preventing the leakage of the oil between the wall of the housing 30 and the wall of the oil circulation line or the oil tank. A cover 48 is coupled on the housing 30 for protecting the internal components such as the UV diode 32, the photodiode 38 and the color sensor 34.

The oil oxidation monitoring device according to the above-described embodiments of the present invention can be variously designed with different variants, regardless of whether the optical fibers are provided or not, or whether the monitoring device is integrated with the oil circulation line (or the oil tank) or not.

Figure 4A:
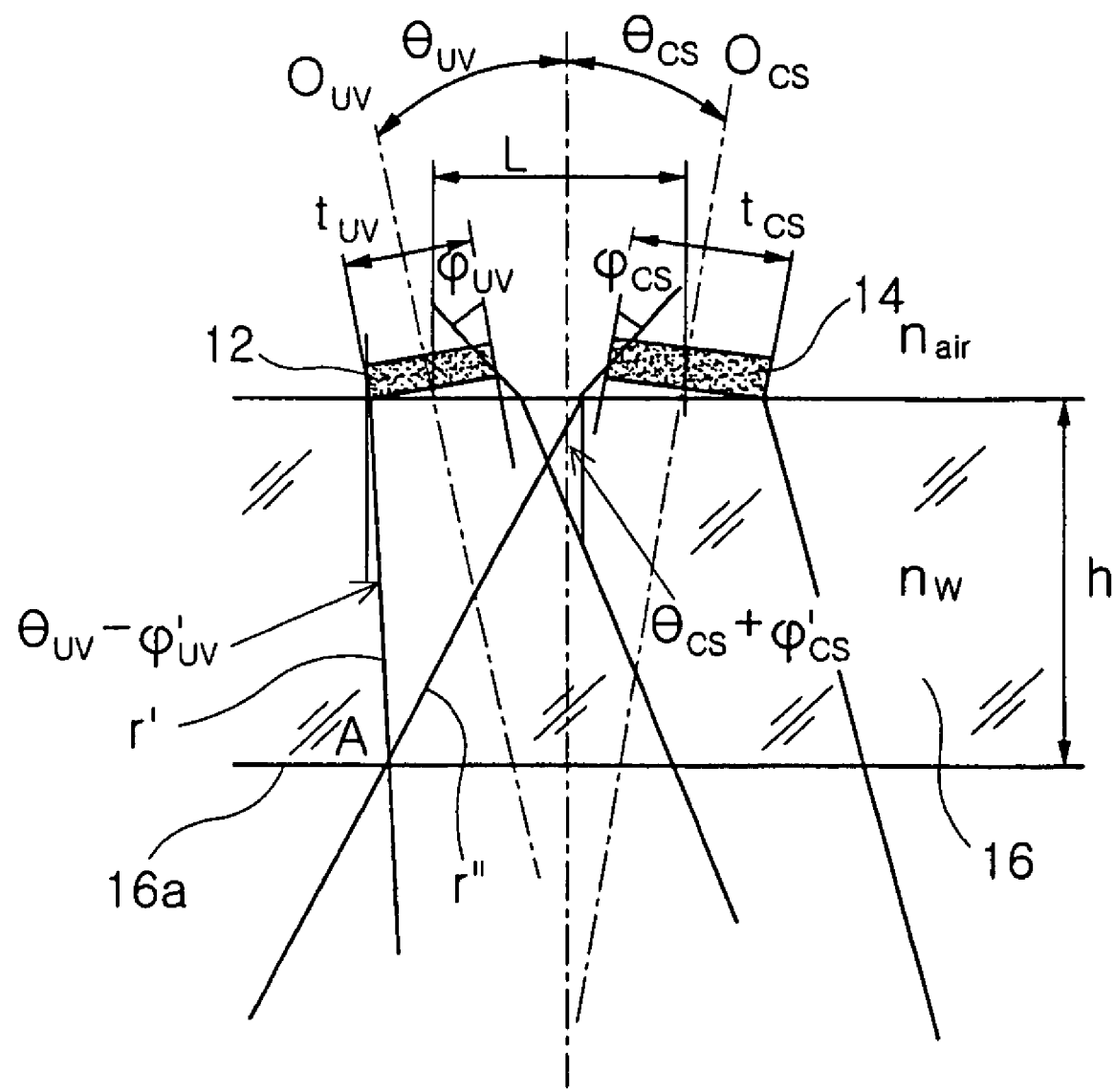
FIG. 4A is a schematic view showing a relationship between aperture angles of a UV emitting means and a color sensing means and a thickness of an optical window in an oil oxidation monitoring device depicted in FIG. 2.

FIG. 4A is a schematic view showing the relationship between aperture angles of the UV emitting means and the color sensing means and a thickness of the optical window in the oil oxidation monitoring device depicted in FIG. 2. An optimal thickness h of the optical window 16 made from optical glass with a refractive index $n_w$ depends upon a distance L between the centers of the UV emitting means 12 and the color sensing means 14, an aperture angle $\phi_{UV}$ and an emitting width $t_{UV}$ of the UV emitting means 12, and an aperture angle $\phi_{CS}$ and a receiving width $t_{CS}$ of the color sensing means 14. These parameters should be matched so that the color sensing means 14 receives as much fluorescence emission of the oil as possible, thereby increasing the sensitivity of the monitoring device. To achieve this, it is preferable that the aperture of the color sensing means 14 is larger than that of the UV emitting means 12 and an extreme ray r' in the emitting range of the UV emitting means 12 is crossed with an extreme ray r in the sensing range of the color sensing means 14 at a point A on the boundary surface 16a of the optical window 16. Under these conditions, the thickness h of the optical window 16 could be calculated by the following equation (1).

$$h = \frac{t_{CS}\left[\frac{1}{2\cos\theta_{CS}} - \cos\theta_{CS} - \sin\theta_{CS}\cdot\tan(\theta_{CS}+\varphi'_{CS})\right]}{\tan(\theta_{UV}-\varphi'_{UV})+\tan(\theta_{CS}+\varphi'_{CS})} \quad \text{Eq. (1)}$$

$$\varphi'_{UV} = \arcsin\frac{n_{air}\cdot\sin\varphi_{UV}}{n_W}, \varphi'_{CS} = \arcsin\frac{n_{air}\cdot\sin\varphi_{CS}}{n_W}$$

wherein $\theta_{UV}$ is an angle between a vertical axis V and an optical axis $O_{UV}$ of the UV emitting means 12, $\theta_{CS}$ is an angle between the vertical axis V and an optical axis $O_{CS}$ of the color sensing means 14, and $n_{air}$ is a refractive index of air.

Figure 4B:
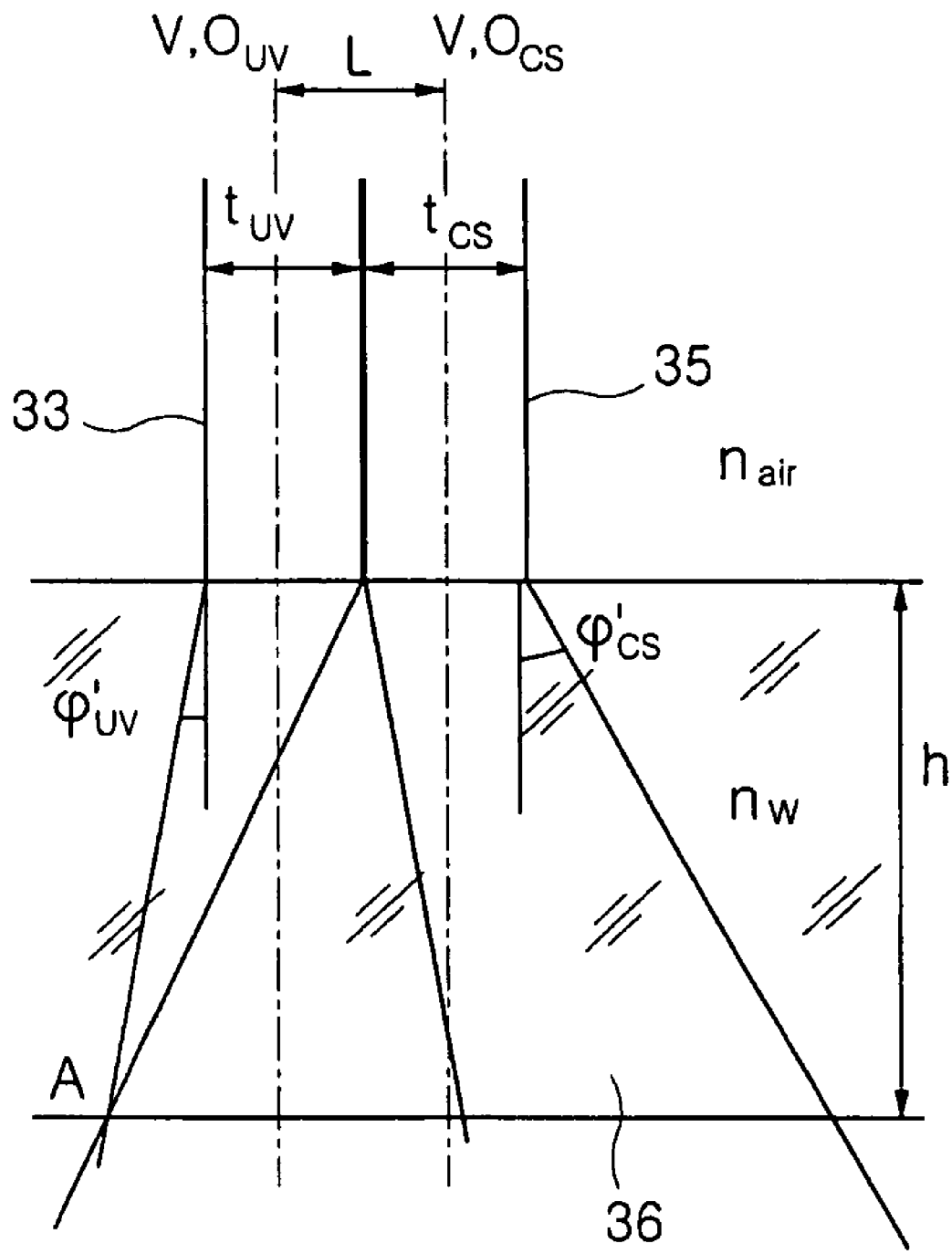
FIG. 4B is a schematic view showing a relationship between aperture angles of a UV emitting means and a color sensing means and a thickness of an optical window in an oil oxidation monitoring device depicted in FIG. 3.

FIG. 4B is a schematic view showing the relationship between aperture angles of the UV emitting means and the color sensing means and a thickness of the optical window in the oil oxidation monitoring device depicted in FIG. 3, wherein the angle between the vertical axis V and the optical axis $O_{UV}$ of the UV emitting means 12 and the angle between the vertical axis V and the optical axis $O_{CS}$ of the color sensing means 14 are all zero ($\theta_{UV}=\theta_{CS}=0$, see FIG. 4A). In addition, the distance L between the centers of the UV emitting means 12 and the color sensing means 14, the emitting width $t_{UV}$ of the first optical fiber 33 and the receiving width $t_{CS}$ of the second optical fiber 35 are all the same. Under these conditions, the above equation (1) can be represented as the following equation (2).

$$h = \frac{t_{uv}}{\tan\varphi'_{cs}-\tan\varphi'_{UV}} \quad \text{Eq. (2)}$$

For example, if each diameter of the first and second optical fibers 33 and 35 is 1 mm, then the aperture angle $\phi_{UV}$ of the first optical fiber 33 is 15°, the aperture angle $\phi_{CS}$ of the second optical fiber 35 is 30°, and the thickness h of the optical window 36 made from the optical glass with the refractive index of 1.5 would be about 6 mm according to the above equation (2).

Although it is depicted in FIGS. 3 and 4B that the first optical fiber 33 and the second optical fiber 35 are provided by one and arranged in parallel with each other, it is certainly not restricted thereto. The first optical fiber 33 may be provided by one, while a plurality of second optical fibers 35 may be provided as they surround the first optical fiber 33. In this case, the larger amount of the fluorescence emission passing through the optical window 36 is transmitted to the color sensor 34 via the second optical fibers 35, thereby achieving a higher optical output.

An oil oxidation monitoring method will now be described below with reference to FIGS. 5 to 8.

Figure 5:
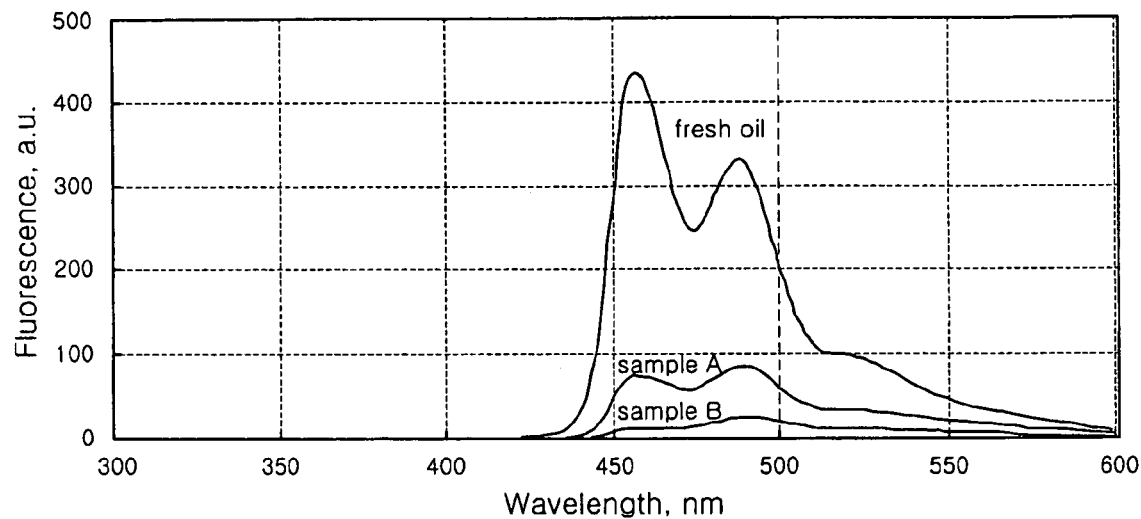
FIG. 5 shows graphs of fluorescence emission spectrums of fresh hydraulic oil and two used hydraulic oil samples.

FIG. 5 shows graphs of fluorescence emission spectrums of fresh hydraulic oil and two used hydraulic oil samples. The used oil samples A and B are taken from a real hydraulic system in the course of its operation. The oxidation level of the oil sample B is higher than that of the oil sample A. Spectrums are measured at an excitation wavelength of 300 nm with a multifrequency cross-correlation phase and modulation fluorometer. As shown in FIG. 5, as the oil oxidizes from the fresh oil to the oil samples A and B, there is an increase in the ratio of the fluorescence emission intensity in a green wavelength band of 470~550 nm to the fluorescence emission intensity in a blue wavelength band of 430~470 nm. In other words, the fluorescence emission spectrum is shifted to the relatively long wavelength band as the oil oxidizes. Therefore, such a shift phenomenon of the spectrum can be used to evaluate the oil oxidation. At this time, there is no need to take into account of the oil absorption of optical radiation.

The above spectrum shift can be estimated as the ratio of the fluorescence intensity $I_{\Delta\lambda long}$ in the relatively long wavelength band to the fluorescence intensity $I_{\Delta\lambda short}$ in the relatively short wavelength band, which is defined as the fluorescence emission ratio (FER).

$$FER = \frac{I_{\Delta\lambda long}}{I_{\Delta\lambda short}} \quad \text{Eq. (3)}$$

To measure the fluorescence intensities in the short and long wavelength bands, a photoreceiver may be used as the color sensor, which detects the light intensity in three wavelength bands—red, green and blue (RGB).

Figure 6:
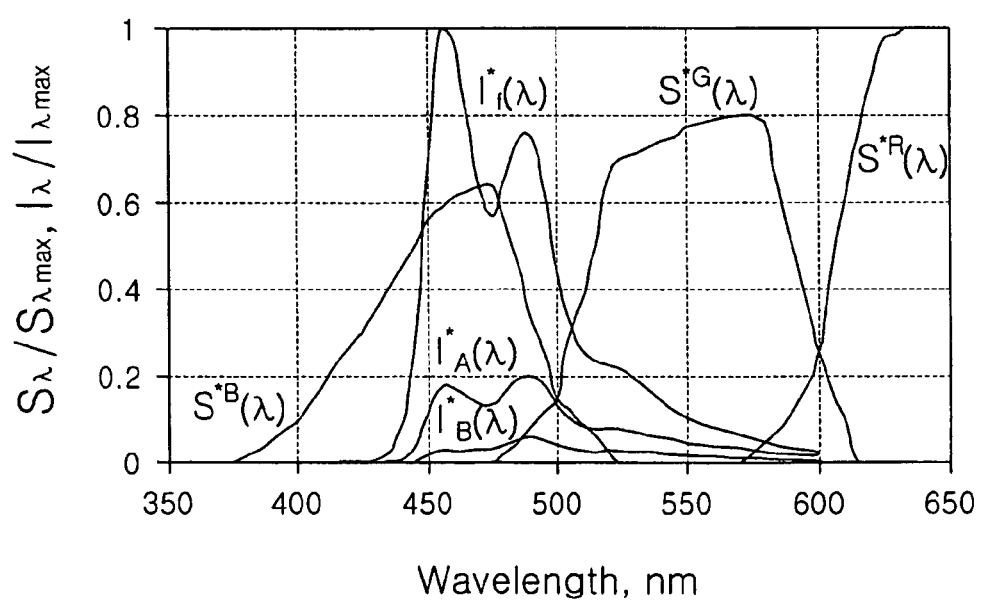
FIG. 6 shows graphs of a relative spectral sensitivity of the color sensor and a relative spectral fluorescence emission intensity in red, green and blue wavelength bands with respect to fresh oil and two used oil samples.

FIG. 6 shows graphs of a relative spectral sensitivity of the color sensor and a relative spectral fluorescence emission intensity in red, green and blue wavelength bands with respect to the fresh oil and two used oil samples. In FIG. 6, $S_\lambda/S_{\lambda max}$ means the relative spectral sensitivity and $I_\lambda/I_{\lambda max}$ means the relative spectral fluorescence emission intensity. $S^{*R}(\lambda)$, $S^{*G}(\lambda)$ and $S^{*B}(\lambda)$ represent the values corresponding to the red, green and blue wavelength bands, respectively. Further, $I^*_f(\lambda)$, $I^*_A(\lambda)$ and $I^*_B(\lambda)$ represent the values corresponding to the fresh oil, oil sample A and oil sample B, respectively.

Figure 7:
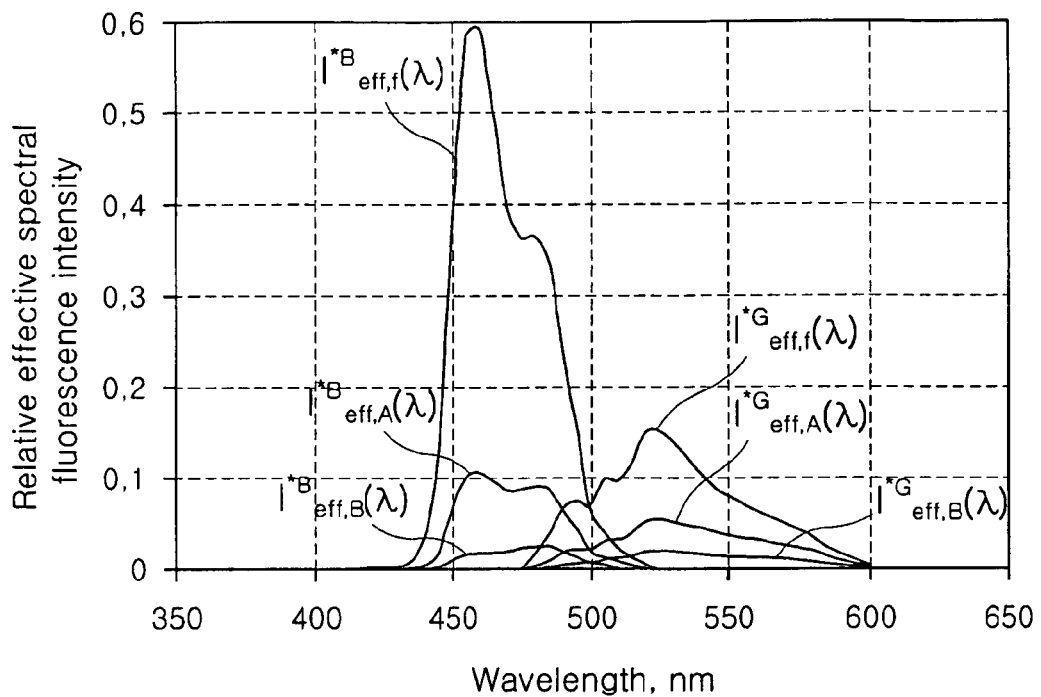
FIG. 7 shows graphs of a relative effective spectral fluorescence intensity for fresh oil and two used oil samples in green and blue wavelength bands.

FIG. 7 shows graphs of a relative effective spectral fluorescence intensity for fresh oil and two used oil samples in the green and blue wavelength bands. $I^{*G}_{eff,f}(\lambda)$ and $I^{*B}_{eff,f}(\lambda)$ represent the values corresponding to fresh oil in the green and blue wavelength bands, respectively. $I^{*G}_{eff,A}(\lambda)$ and $I^{*B}_{eff,A}(\lambda)$ represent the values corresponding to used oil sample A in the green and blue wavelength bands, respectively. $I^{*G}_{eff,B}(\lambda)$ and $I^{*B}_{eff,B}(\lambda)$ represent the values corresponding to used oil sample B in the green and blue wavelength bands, respectively. Because the values of the relative effective spectral fluorescence intensity for fresh oil and two used oil samples A and B in the red wavelength band are nearly zero, they are not shown in FIG. 7.

The effective spectral fluorescence intensity, which is converted to an electrical signal by the color sensor, is derived by multiplying the spectral fluorescence intensity $I(\lambda)$ and the relative spectral sensitivity $S(\lambda)$ of the color sensor, as shown in the following equation (4).

$$I_{eff}(\lambda) = I(\lambda) \cdot S(\lambda) \quad \text{Eq. (4)}$$

Based on the above equation (4), the relative effective spectral fluorescence intensity for fresh oil in the red, green and blue wavelength bands is calculated as follows.

$$I^{*R}_{eff,f}(\lambda) = I^*_f(\lambda) \cdot S^{*R}(\lambda) \quad \text{Eq. (5)}$$

$$I^{*G}_{eff,f}(\lambda) = I^*_f(\lambda) \cdot S^{*G}(\lambda) \quad \text{Eq. (6)}$$

$$I^{*B}_{eff,f}(\lambda) = I^*_f(\lambda) \cdot S^{*B}(\lambda) \quad \text{Eq. (7)}$$

Based on the above equation (4), the relative effective spectral fluorescence intensity for used oil sample A in the red, green and blue wavelength bands is calculated as follows.

$$I^*_{\text{eff},A}{}^R(\lambda)=I^*_A(\lambda)\cdot S^{*R}(\lambda) \qquad \text{Eq. (5)}$$

$$I^*_{\text{eff},A}{}^G(\lambda)=I^*_A(\lambda)\cdot S^{*G}(\lambda) \qquad \text{Eq. (6)}$$

$$I^*_{\text{eff},A}{}^B(\lambda)=I^*_A(\lambda)\cdot S^{*B}(\lambda) \qquad \text{Eq. (7)}$$

Based on the above equation (4), the relative effective spectral fluorescence intensity for used oil sample B in the red, green and blue wavelength bands is calculated as follows.

$$I^*_{\text{eff},B}{}^R(\lambda)=I^*_B(\lambda)\cdot S^{*R}(\lambda) \qquad \text{Eq. (5)}$$

$$I^*_{\text{eff},B}{}^G(\lambda)=I^*_B(\lambda)\cdot S^{*G}(\lambda) \qquad \text{Eq. (6)}$$

$$I^*_{\text{eff},B}{}^B(\lambda)=I^*_B(\lambda)\cdot S^{*B}(\lambda) \qquad \text{Eq. (7)}$$

An output current from the color sensor is proportional to the effective fluorescence intensity and is calculated by the following equation (14).

$$J = S_{\lambda\max}\cdot I_{\lambda\max}\int_{\lambda_1}^{\lambda_3}I^*_{\text{eff}}(\lambda)d\lambda \qquad \text{Eq. (14)}$$

Figure 8:
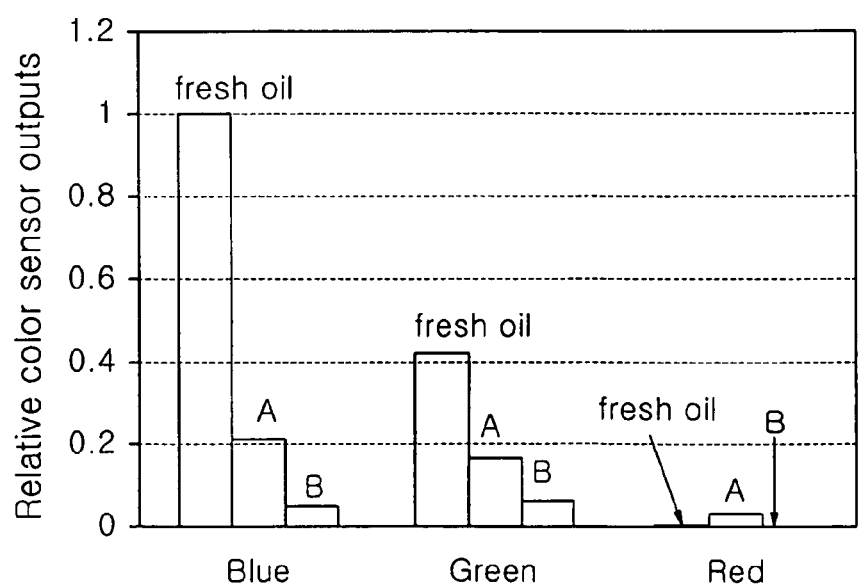
FIG. 8 shows graphs of a relative color sensor output for fresh oil and two used oil samples.

FIG. 8 shows graphs of a relative color sensor output for fresh oil and two used oil samples. The graphs show that the outputs for fresh oil and two used oil samples A and B in the red wavelength band are nearly zero. However, the outputs in the blue and green wavelength bands decrease as the oil oxidizes. The critical point derived from the graphs in FIG. 8 is that the proportions of the outputs in the blue and green wavelength bands occupy in the total output (sum of each output in the red, green and blue wavelength bands) are changed relatively. More specifically, the proportion of the output in the blue wavelength band occupies in the total output is about 70% for fresh oil, about 50% for used oil sample A, and about 40% for used oil sample B. That is, as the oil oxidizes, the proportion of the output in the blue wavelength band occupies in the total output decreases. On the contrary, the proportion of the output in the green wavelength band occupies in the total output is about 30% for fresh oil, about 45% for used oil sample A, and about 60% for used oil sample B. That is, as the oil oxidizes, the proportion of the output in the green wavelength band occupies in the total output increases.

This phenomenon is evaluated by the FER parameter, which is defined by the ratio of the color sensor output ($J_G=J_{\Delta\lambda long}$) in the green wavelength band to the color sensor output ($J_B=J_{\Delta\lambda short}$) in the blue wavelength band, or by the ratio of the output voltage ($U_{\Delta\lambda long}$) of the invented monitoring device in relatively long wavelength band to the output voltage ($U_{\Delta\lambda short}$) in relatively short wavelength band, as follows:

$$FER = \frac{J_G}{J_B} = \frac{J_{\Delta\lambda long}}{J_{\Delta\lambda short}} = \frac{U_{\Delta\lambda long}}{U_{\Delta\lambda short}} \qquad \text{Eq. (15)}$$

In this embodiment, since the oil fluorescence intensity in the red wavelength band is so weak, the green wavelength band is adopted as the long wavelength band and the blue wavelength band is adopted as the short wavelength band, although not restricted thereto. In other words, the FER may be calculated by diversely selecting relatively long and short wavelength bands among the red, green and blue wavelength bands (e.g., the red wavelength band is adopted as the long wavelength band and the green wavelength band is adopted as the short wavelength band). The change in the FER in the course of oxidation of hydraulic oil is depicted in FIG. 9.

The method of monitoring the oxidation of oil stored in a certain machine by using the above device comprises the following steps: irradiating ultraviolet light from the UV emitting means into oil to be detected; measuring the fluorescence emission intensity from oil in the red, green and blue wavelength bands by using the outputs $J_R$, $J_G$ and $J_B$ of the color sensing means; determining one output in relatively long wavelength band and the other output in relatively short wavelength band among the outputs $J_R$, $J_G$ and $J_B$ of the color sensing means; calculating the FER from the above equation (15); and monitoring the change in the FER in the course of the machine operation.

Figure 9:
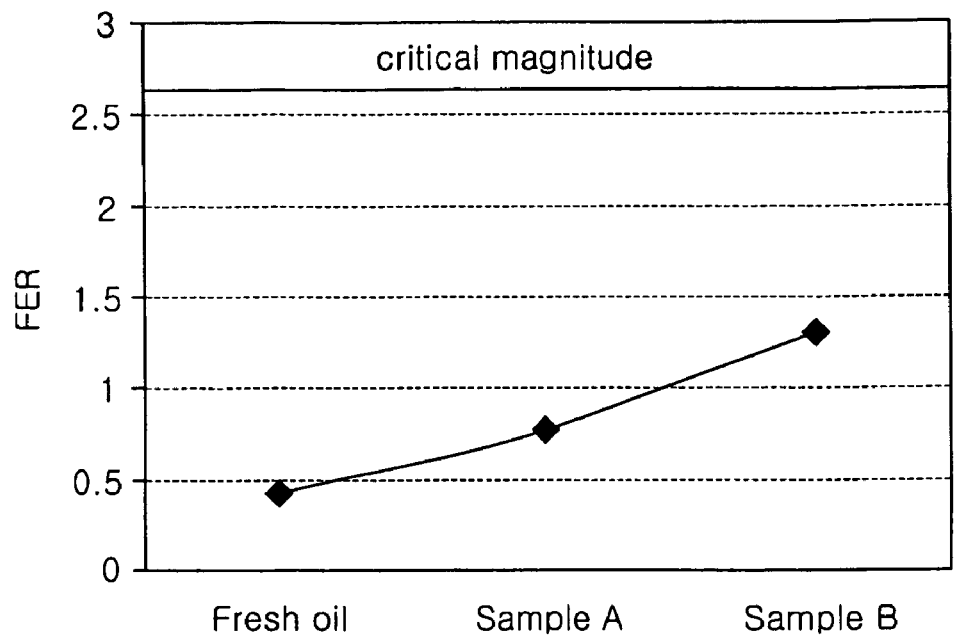
FIG. 9 shows a graph of a change in a fluorescence emission ratio (FER) in the course of oxidation of hydraulic oil.

During the steps of calculating the FER and monitoring its change, the control portion C (see FIG. 2) determines whether the value of the FER reaches a predetermined critical magnitude (see FIG. 9). If the value of the FER is below the critical magnitude, the control portion C determines that oil is in a good condition. If the value of the FER is above the critical magnitude, the control portion C determines that oil oxidizes to a poor condition and then operates the displaying means D (e.g., a digital indicator, an alarming lamp, etc.) (see FIG. 2) to indicate the necessity of replacing the used oil with new one.

Figure 10:
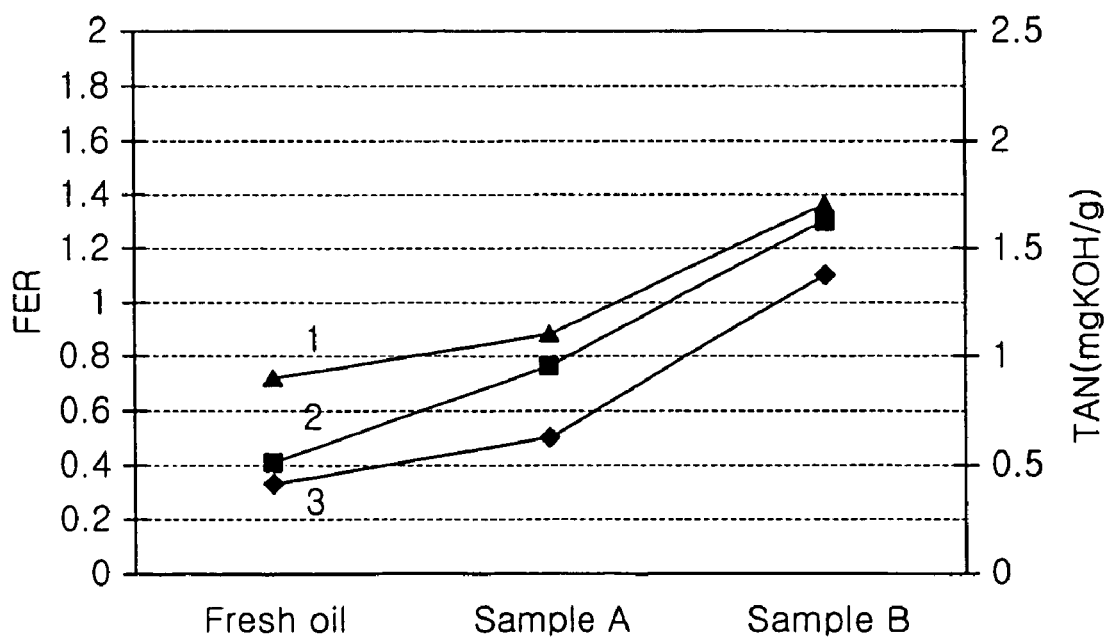
FIG. 10 shows graphs of FER data (curve 1) calculated by using a monitoring device and a method of the present invention, theoretical FER data (curve 2) and TAN (curve 3) for fresh hydraulic oil and two used hydraulic oil samples.

FIG. 10 shows graphs of FER data (curve 1) calculated by using the monitoring device and method of the present invention, theoretical FER data (curve 2) and TAN (curve 3) for fresh hydraulic oil and two used hydraulic oil samples.

Figure 11A:
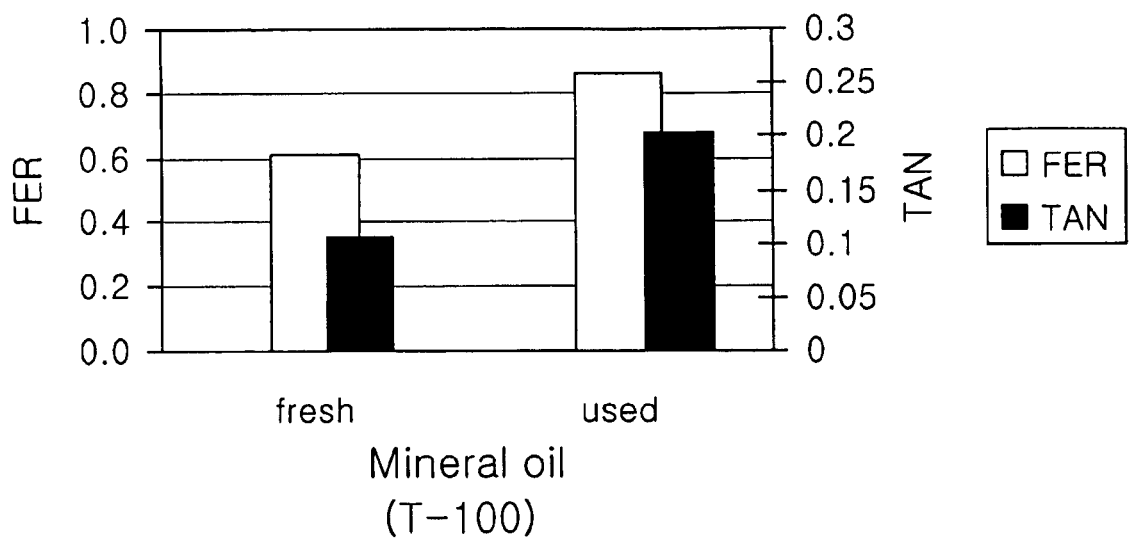
FIGS. 11A to 11C show graphs of comparing FER data calculated by using a monitoring device and a method of the present invention and TAN for fresh and used mineral oil.
Figure 11B:
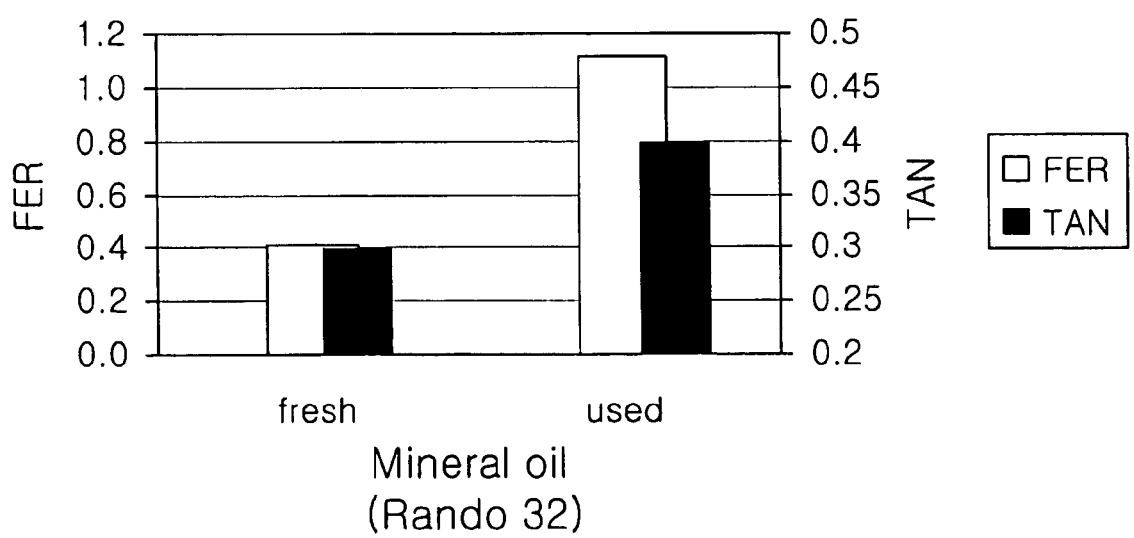
Figure 11C:
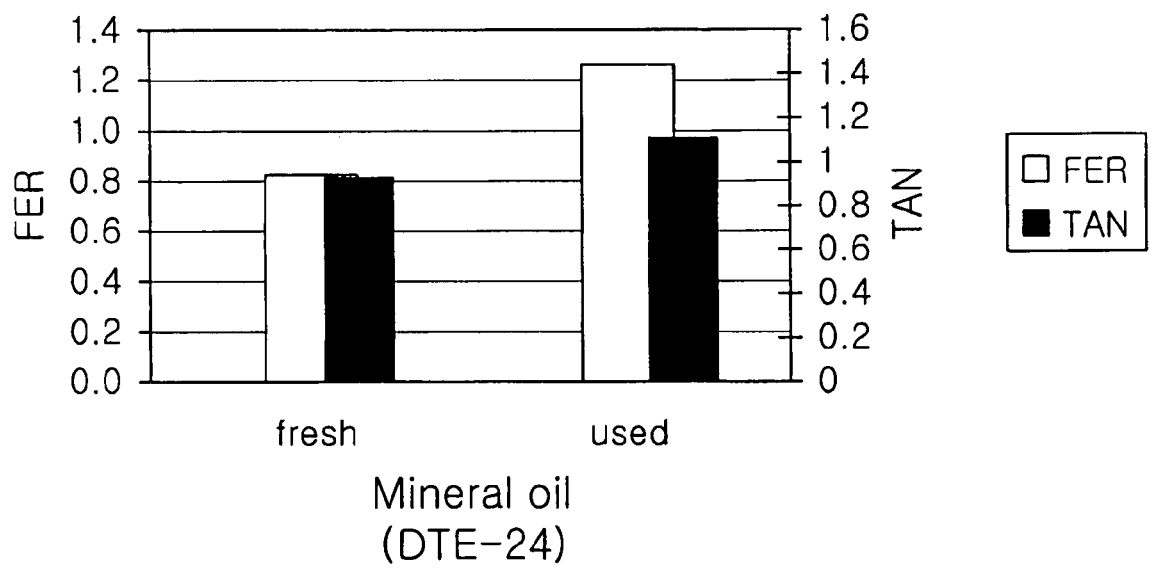
Figure 11D:
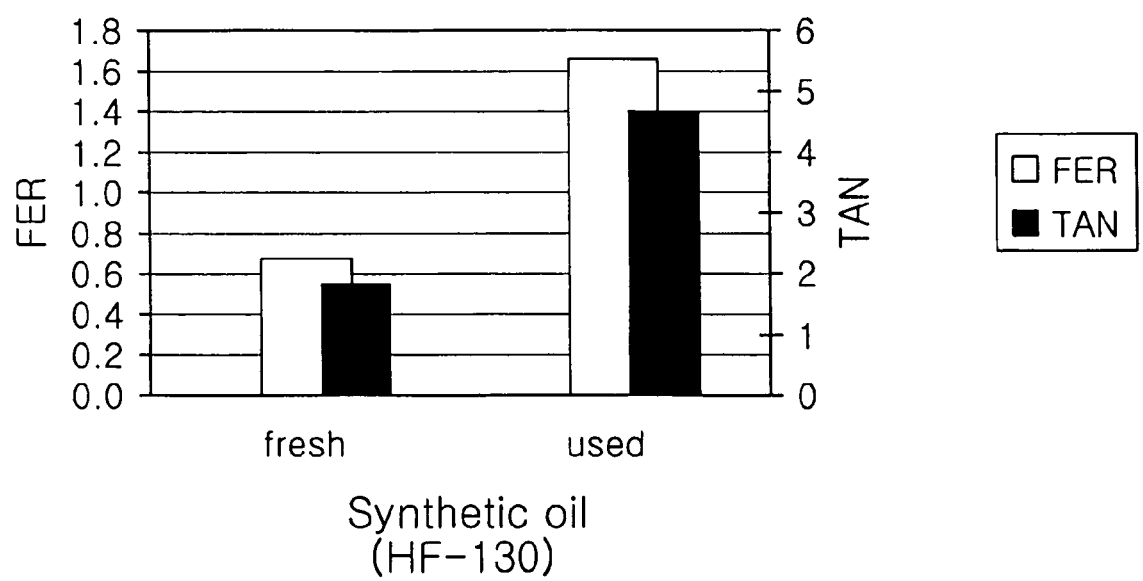
FIG. 11D shows graphs of comparing FER data calculated by using a monitoring device and a method of the present invention and TAN for fresh and used synthetic oil.

FIGS. 11A to 11C show graphs of comparing FER data calculated by using the monitoring device and method of the present invention and TAN for fresh and used mineral oil. The tested mineral oil is the part number "T-100", "Rando 32" and "DTE-24" manufactured by Teresso Inc. FIG. 11D shows graphs of comparing FER data calculated by using the monitoring device and method of the present invention and TAN for fresh and used synthetic oil. The tested synthetic oil is the part number "HF-130" manufactured by Teresso Inc.

As apparently known from FIGS. 10 to 11D, the values of FER calculated by using the monitoring device and method of the present invention for real oil products on the market have a considerably high correlation with the results of measuring TAN, which is presently the most used method of detecting the oil oxidation.

As described above in detail, the method and device for monitoring oil oxidation according to the present invention is to use the phenomenon of that the fluorescence emission intensity increases as oil oxidizes. Especially, the monitoring method comprises a convenient process of: measuring the fluorescence emission intensity from oil in the red, blue and green wavelength bands by using the color sensor; calculating the ratio of the fluorescence emission intensity in relatively long wavelength band to the fluorescence emission intensity in relatively short wavelength band; and monitoring the change in the calculated ratio.

Further, the inventive monitoring device is configured to use a common available and cheap color sensor. Thus, it is more effective in cost and can be mounted to mechanical devices such as a car engine so as to measure the oil oxidation in real time.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes, which come within the equivalent meaning and range of the claims, are to be embraced within their scope.

What is claimed is:

1. A method of monitoring the oxidation of a lubricant in real time, comprising the steps of:
   (a) irradiating a lubricant to be monitored with an ultraviolet light;
   (b) measuring a fluorescence emission intensity from the lubricant in red, green and blue wavelength bands;
   (c) determining a first value of fluorescence intensity measured in the green wavelength band of 470 nm to 550 nm and a second value of fluorescence intensity measured in the blue wavelength band of 430 nm to 470 nm among the fluorescence emission intensity measured in the red, green and blue wavelength bands;
   (d) calculating a fluorescence emission ratio by taking a ratio of the first value measured in the green wavelength band to the second value measured in the blue wavelength band;
   (e) monitoring a change in the fluorescence emission ratio in course of oxidation of the lubricant;
   (f) determining whether the fluorescence emission ratio reaches a predetermined critical magnitude; and
   (g) indicating the necessity of replacing the lubricant when the fluorescence emission ratio reaches the critical magnitude.

2. A device of monitoring the oxidation of a lubricant in real time, comprising:
   a housing mounted to a wall of a unit containing a lubricant to be monitored;
   a transparent optical window disposed in the housing, the optical window having a boundary surface configured to be in contact with the lubricant;
   a UV diode provided inside the housing for irradiating an ultraviolet light into the lubricant through the optical window;
   a color sensor provided inside the housing for detecting a fluorescence light emission of the lubricant, the fluorescence light emission passing through the optical window in red, green and blue wavelength bands, and measuring a fluorescence emission intensity; and
   a control portion for determining a first value of fluorescence intensity measured in the green wavelength band of 470 nm to 550 nm and a second value of fluorescence intensity measured in the blue wavelength band of 430 nm to 470 nm among the fluorescence emission intensity measured in the red, green and blue wavelength bands by the color sensor, the control portion being configured to calculate a ratio of the first value measured in the green wavelength band to the second value measured in the blue wavelength band, the control portion further being configured to monitor a change in the ratio;
   wherein a thickness of the optical window is calculated from the following ecluation:

$$h = \frac{L + \frac{t_{UV}}{2\cos\theta_{UV}} + t_{CS}\left[\frac{1}{2\cos\theta_{CS}} - \cos\theta_{CS} - \sin\theta_{CS} \cdot \tan(\theta_{CS} + \varphi'_{CS})\right]}{\tan(\theta_{UV} - \varphi'_{UV}) + \tan(\theta_{CS} + \varphi'_{CS})}$$

$$\varphi'_{UV} = \arcsin\frac{n_{air} \cdot \sin\varphi_{UV}}{n_W}, \quad \varphi'_{CS} = \arcsin\frac{n_{air} \cdot \sin\varphi_{CS}}{n_W}$$

wherein h means the thickness of the optical window, L means a distance between the centers of the UV diode and the color sensor, $\theta_{UV}$ means an angle between a vertical axis and an optical axis of the UV diode $\theta_{CS}$ means an angle between the vertical axis and an optical axis of the color sensor, $\phi_{UV}$ means an aperture angle of the UV diode, $\phi_{CS}$ means an aperture angle of the color sensor, $t_{UV}$ means an emitting width of the UV diode, $t_{CS}$ means a receiving width of the color sensor, $n_w$, means a refractive index of the optical window, and $n_{air}$ means a refractive index of air.

3. The device of claim 2, wherein a first optical fiber connected to the UV diode is provided inside the housing, the first optical fiber being configured to transmit the ultraviolet light from the UV diode to the optical window.

4. The device of claim 3, wherein a ball lens is provided between the UV diode and an end of the first optical fiber, the ball lens being configured to focus the ultraviolet light from the UV diode on the end of the first optical fiber.

5. The device of claim 2, wherein at least one second optical fiber connected to the color sensor is provided inside the housing, the second optical fiber being configured to transmit the fluorescence light emission of the lubricant to the color sensor, the fluorescence light emission passing through the optical window.

6. The device of claim 2, wherein an oleophobic material is coated on the boundary surface of the optical window for preventing an adherence of contaminants to the boundary surface.

7. The device of claim 6, wherein the oleophobic material is fluorosilane polymer carried in hydrofluoroether solvent.

8. The device of claim 2, wherein the device further comprises a displaying means electrically connected to the control portion,
   and wherein the control portion determines whether the ratio of the first value measured in the green wavelength band to the second value measured in the blue wavelength band reaches a predetermined critical magnitude,
   if the ratio reaches the critical magnitude, the control portion operates the displaying means to indicate the necessity of replacing the lubricant.

* * * * *